United States Patent
Bardhan Roy et al.

(10) Patent No.: US 11,904,357 B2
(45) Date of Patent: Feb. 20, 2024

(54) MICROMACHINED ULTRASONIC TRANSDUCERS WITH NON-COPLANAR ACTUATION AND DISPLACEMENT

(71) Applicant: GE Precision Healthcare LLC, Wauwatosa, WI (US)

(72) Inventors: Rupak Bardhan Roy, Nice (FR); Frederic Lanteri, Le Cannet (FR); Edouard Da Cruz, Nice (FR); Flavien Daloz, Biot (FR); Jean Francois Gelly, Mougins (FR)

(73) Assignee: GE Precision Healthcare LLC, Waukesha, WI (US)

( * ) Notice: Subject to any disclaimer, the term of this patent is extended or adjusted under 35 U.S.C. 154(b) by 388 days.

(21) Appl. No.: 16/881,341

(22) Filed: May 22, 2020

(65) Prior Publication Data

US 2021/0362188 A1    Nov. 25, 2021

(51) Int. Cl.
*B06B 1/02*    (2006.01)
*A61B 8/00*    (2006.01)

(52) U.S. Cl.
CPC .......... *B06B 1/0292* (2013.01); *A61B 8/4494* (2013.01); *B06B 2201/76* (2013.01)

(58) Field of Classification Search
CPC ..... B06B 1/0292; B06B 1/02; G01S 15/8909; H01L 21/449; B81C 1/00158; B81C 1/00373
See application file for complete search history.

(56) References Cited

U.S. PATENT DOCUMENTS

| | | | |
|---|---|---|---|
| 8,526,271 B2 | 9/2013 | Huang | |
| 10,092,270 B2 | 10/2018 | Dirksen | |
| 2011/0040189 A1 | 2/2011 | Petruzzello et al. | |
| 2012/0086087 A1 | 4/2012 | Fitzpatrick | |
| 2012/0103096 A1* | 5/2012 | Kandori | B81B 3/0021 73/632 |
| 2015/0009778 A1* | 1/2015 | Kandori | G01H 11/06 310/300 |
| 2016/0199030 A1 | 7/2016 | Patil et al. | |
| 2017/0165715 A1* | 6/2017 | Sudol | G01N 29/262 |

(Continued)

FOREIGN PATENT DOCUMENTS

WO    WO 2016/080931    *    5/2016

OTHER PUBLICATIONS

Jeff McLean, et al. Woodruff School of Mechanical Engineering Georgia Institute of Technology, "CMUTS With Dual Electrode Structure For Improved Transmit And Receive Performance", 2004 IEEE Ultrasonics Symposium, pp. 501-504. (Presented Sep. 2004; Published in IEEE (https://ieeexplore.ieee.org/document/1593388) on Feb. 13, 2006).

*Primary Examiner* — Wasiul Haider
(74) *Attorney, Agent, or Firm* — McAndrews, Held & Malloy, Ltd.; Daniel Bissing; David Bates

(57) ABSTRACT

A micromachined ultrasonic transducers with non-coplanar actuation and displacement comprising a plate with a protruding center mass, a substrate with a center depression configured to accept the center mass, a first electrode coupled to a non-horizontal edge surface of the center mass, and a second electrode coupled to a non-horizontal edge surface of the center depression. The plate may be coupled to the substrate at least along an outer perimeter area of the plate and the substrate.

20 Claims, 14 Drawing Sheets

(56) References Cited

U.S. PATENT DOCUMENTS

2017/0232474 A1\* 8/2017 Oralkan .................. B81C 3/001
                                                          310/309
2017/0320091 A1   11/2017 Budzelaar \* cited by examiner

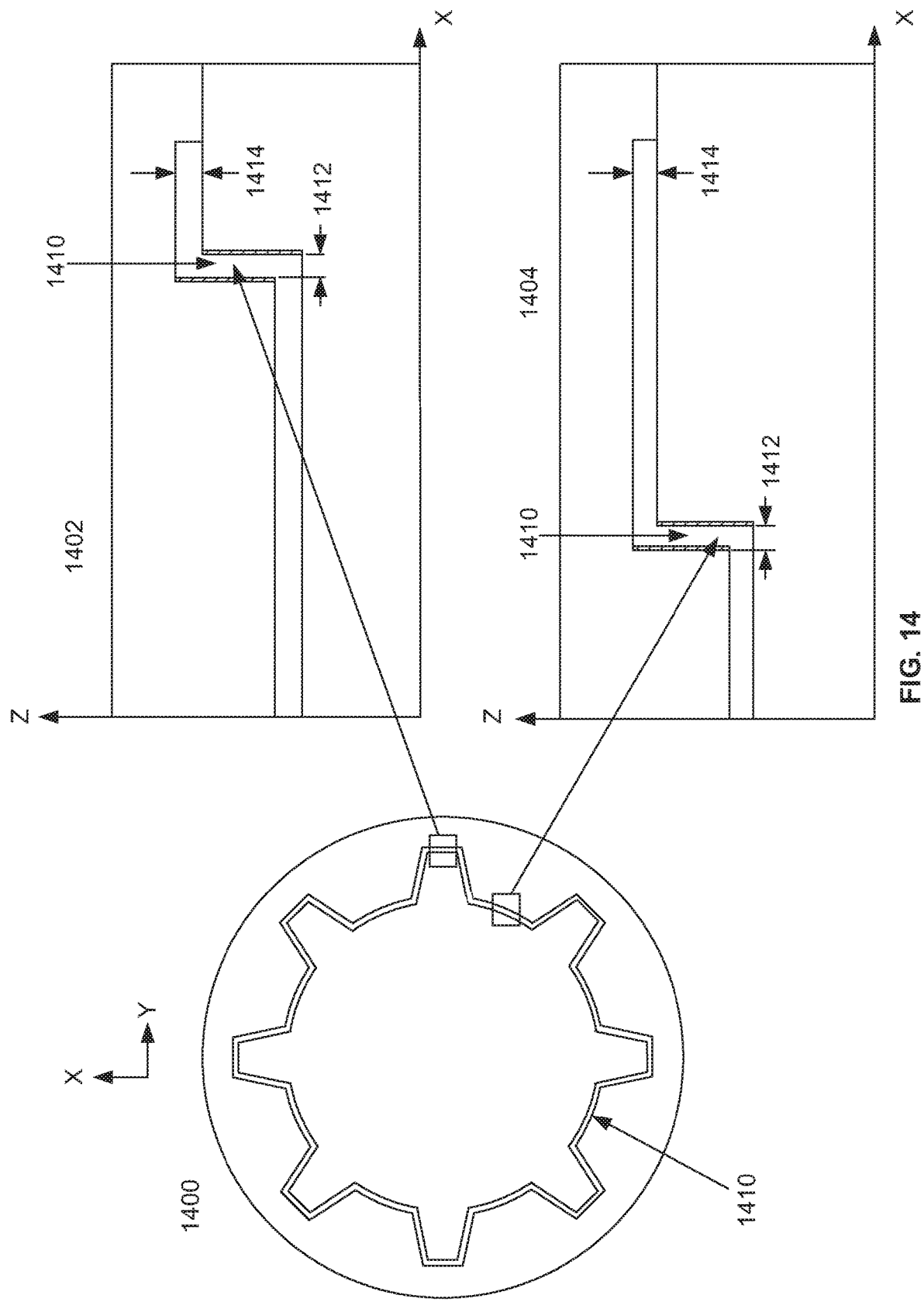

MICROMACHINED ULTRASONIC TRANSDUCERS WITH NON-COPLANAR ACTUATION AND DISPLACEMENT

FIELD

Certain embodiments relate to a transducer. More specifically, certain embodiments relate to micromachined ultrasonic transducers with non-coplanar actuation and displacement.

BACKGROUND

An ultrasound device may be used for imaging targets such as organs and soft tissues in a human body, as well non-human targets. For example, an ultrasound device may be used for applications such as ultrasound/acoustic sensing, non-destructive evaluation (NDE), ultrasound therapy (e.g., High Intensity Focused Ultrasound (HIFU)), etc., in addition to ultrasound imaging of humans, animals, etc.

Ultrasound devices may use real time, non-invasive high frequency sound waves to produce a series of two-dimensional (2D) and/or three-dimensional (3D) images. The sound waves may be transmitted by a transmit transducer, and the reflections of the transmitted sound waves may be received by a receive transducer. The received sound waves may then be processed to display an image of the target. A conventional capacitive micromachined ultrasound transducer (CMUT) that is used as a transmit transducer and/or a receive transducer may comprise a top electrode and a bottom electrode, where the top electrode may move due to electrical signals to generate sound waves, or move due to receiving sound waves to generate electrical signals that can be processed. The top electrode and the bottom electrode may be separated by a gap, where the gap may comprise some level of vacuum or the gap may be filled with, for example, air.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or a method are provided for a micromachined ultrasonic transducers with non-coplanar actuation and displacement, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

BRIEF DESCRIPTION OF SEVERAL VIEWS OF THE DRAWINGS

FIG. 14 illustrates another configuration for an example capacitive micromachined ultrasound transducer (CMUT) with non-coplanar actuation and displacement, in accordance with various embodiments.

DETAILED DESCRIPTION

Figure 1:
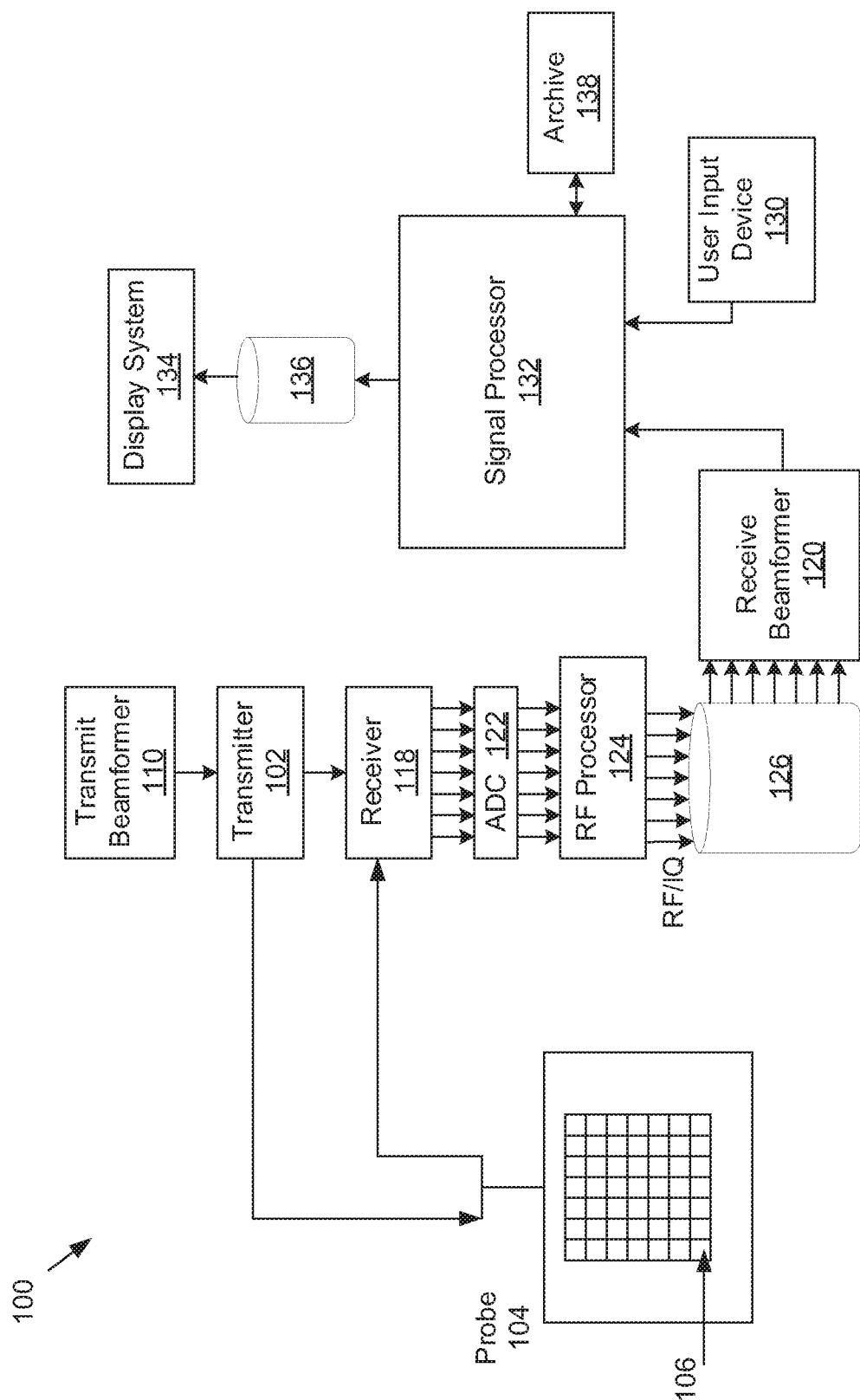
FIG. 1 is a block diagram of an exemplary ultrasound system that may be used in ultrasound imaging, in accordance with various embodiments.

Certain embodiments may be found in a micromachined ultrasonic transducers with non-coplanar actuation and displacement. Various embodiments of the disclosure may use non-coplanar actuation and displacement where actuation is via electrodes that are not coplanar to the membrane displacement direction.

Accordingly, the various embodiments provide for a technical effect of operation by the capacitive micromachined ultrasound tranducer (CMUT) where the electrodes for actuation do not short circuit with each other.

While a CMUT can be used for medical imaging, the CMUT may also be used for various other purposes such as, for example, ultrasound/acoustic sensing, non-destructive evaluation (NDE), ultrasound therapy (e.g., High Intensity Focused Ultrasound (HIFU)), etc., in addition to ultrasound imaging of humans or animals.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. It should be understood that the various embodiments are not limited to the arrangements and instrumentality shown in the drawings. It should also be understood that the embodiments may be combined, or that other embodiments may be utilized and that structural, logical, and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

Additionally, it should be noted that the drawings may not depict objects to scale, but instead strive to present the figures for clarity of explanation.

FIG. 1 is a block diagram of an exemplary ultrasound system that may be used in ultrasound imaging, in accordance with various embodiments. Referring to FIG. 1, there is shown a block diagram of an exemplary ultrasound system 100. The ultrasound system 100 comprises a transmitter 102, an ultrasound probe 104, a transmit beamformer 110, a receiver 118, a receive beamformer 120, A/D converters 122, an RF processor 124, an RF/IQ buffer 126, a user input device 130, a signal processor 132, an image buffer 136, a display system 134, and an archive 138.

The transmitter 102 may comprise suitable logic, circuitry, interfaces and/or code that may be operable to drive the ultrasound probe 104. The ultrasound probe 104 may comprise, for example, a single element CMUT, a 1D array of CMUTs, 2D array of CMUTs, an annular (ring) array of CMUTs, etc. Accordingly, the ultrasound probe 104 may comprise a group of transducer elements 106 that may be, for example, CMUTs. In certain embodiments, the ultrasound probe 104 may be operable to acquire ultrasound image data covering, for example, at least a substantial portion of an anatomy, such as the heart, a blood vessel, or any suitable anatomical structure. Each of the transducer elements 106 may be referred to as a channel.

The transmit beamformer 110 may comprise suitable logic, circuitry, interfaces and/or code that may be operable to control the transmitter 102 that drives the group of transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes can then be received by the transducer elements 106.

The group of transducer elements 106 in the ultrasound probe 104 may be operable to convert the received echoes into analog signals and communicated to a receiver 118. The receiver 118 may comprise suitable logic, circuitry, interfaces and/or code that may be operable to receive the signals from the ultrasound probe 104. The analog signals may be communicated to one or more of the plurality of A/D converters 122.

Accordingly, the ultrasound system 100 may multiplex such that ultrasonic transmit signals are transmitted during certain time periods and echoes of those ultrasonic signals are received during other time periods. Although not shown explicitly, various embodiments of the disclosure may allow simultaneous transmission of ultrasonic signals and reception of echoes from those signals. In such cases, the probe may comprise transmit transducer elements and receive transducer elements.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF data, which may be, for example, I/Q signal data, real valued RF data, etc., may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

Accordingly, various embodiments may have, for example, the RF processor 124 process real valued RF data, or any other equivalent representation of the data, with an appropriate RF buffer 126.

The receive beamformer 120 may comprise suitable logic, circuitry, interfaces and/or code that may be operable to perform digital beamforming processing to sum, for example, delayed, phase shifted, and/or weighted channel signals received from the RF processor 124 via the RF/IQ buffer 126 and output a beam summed signal. The delayed, phase shifted, and/or weighted channel data may be summed to form a scan line output from the receive beamformer 120, where the scan line may be, for example, complex valued or non-complex valued. The specific delay for a channel may be provided, for example, by the RF processor 124 or any other processor configured to perform the task. The delayed, phase shifted, and/or weighted channel data may be referred to as delay aligned channel data.

The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 may comprise a plurality of receive beamformers 120.

The user input device 130 may be utilized to input patient data, scan parameters, settings, select protocols and/or templates, and the like. In an exemplary embodiment, the user input device 130 may be operable to configure, manage, and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include switch(es), button(s), rotary encoder(s), a touchscreen, motion tracking, voice recognition, a mouse device, keyboard, camera, and/or any other device capable of receiving a user directive. In certain embodiments, one or more of the user input devices 130 may be integrated into other components, such as the display system 134 or the ultrasound probe 104, for example. As an example, user input device 130 may comprise a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in a live or off-line operation. In various embodiments, the processed image data can be presented at the display system 134 and/or stored at the archive 138. The archive 138 may be a local archive, a Picture Archiving and Communication System (PACS), or any suitable device for storing images and related information.

The signal processor 132 may comprise one or more central processing units, microprocessors, microcontrollers, and/or the like. The signal processor 132 may be an integrated component, or may be distributed across various locations, for example. In an exemplary embodiment, the signal processor 132 may be capable of receiving input information from the user input device 130 and/or the archive 138, generating an output displayable by the display system 134, and manipulating the output in response to input information from the user input device 130, among other things. The signal processor 132 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates may range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes worth of frames of ultrasound scan data. The frames of ultrasound scan data are stored in a manner to facilitate retrieval thereof according to its order or time of acquisition. The image buffer 136 may be embodied as any known data storage medium.

The display system 134 may be any device capable of communicating visual information to a user. For example, a display system 134 may include a liquid crystal display, a light emitting diode display, and/or any suitable display or displays. The display system 134 can be operable to present ultrasound images and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display. Additionally, while the ultrasound system 100 was described to comprise a receive beamformer 120, an RF processor 124, and a signal processor 132, various embodiments of the disclosure may use various number of processors. For example, various devices that execute code may be referred to generally as processors. Various embodiments may refer to each of these devices, including each of the RF processor 124 and the signal processor 132, as a processor. Furthermore, there may be other processors to additionally perform the tasks described as being performed by these devices, including the receive beamformer 120, the RF processor 124, and the signal processor 132, and all of these processors may be referred to as a "processor" for ease of description.

Certain applications may find it desirable to drive conventional Capacitive Micromachined Ultrasonic Transducers (CMUTs) hard enough so that they operate in collapse mode. That is, the top electrode is driven to the bottom electrode. This may permit the CMUTs to provide higher levels of acoustic power, more linearity and wider bandwidth during operation. However, with conventional CMUTS that have top and bottom electrodes, the top electrode may then contact the bottom electrode, resulting in an electrical short circuit of the electrodes that may cause permanent damage to the structure of the CMUT.

To avoid this problem, one or more insulation layers or bumps have been sandwiched between the bottom electrode and the top electrode. However, this may result in electrical reliability issues due to charging problems caused by trapped charges in the thin dielectric insulation layers. While various efforts have been made to overcome this problem, industrial CMUT devices to date have not been able to overcome the problems associated with operating in collapse mode due to reliability issues. Two most important causes for the trapped charges are the fabrication process CMUT, and strong electrical field in the gap during operation of the CMUT.

Charges can be trapped either on the surface or within a dielectric insulation layer that may be present in a convention CMUT. The trapped charges shield the electrode surface with unintended effects depending on the amplitude and frequency of the drive signal superimposed on the DC bias. Additionally, such charges can cause issues during membrane snapback after collapse.

While some solutions offered both from academics and industry include the use of PostCMUTs, spacers (membrane bumps), extended edge insulator thickness, etc., these approaches merely localized the charging issue to smaller regions. The charge trapping still occurs, and, therefore, the problem still exists.

Various embodiments of the disclosure provide for a novel Capacitive Micromachined Ultrasonic Transducer where the actuation may be, for example, orthogonal to the direction of membrane vibration. In a conventional structure the bias and AC signal are provided to an electrode that is attached to a membrane. Accordingly, the electrode moves along the same direction with the displacement of the membrane, which has a direct consequence of collapse. The current structure and actuation process have the advantage of avoiding mechanical collapse even after $1/3^{rd}$ of the gap height has been traversed, hence avoiding the collapse voltage constraint found in conventional CMUTs. The actuation may be achieved, for example, by applying bias and AC signal orthogonally to the direction of displacement.

Conventional Capacitive Micromachined Ultrasonic Transducers (CMUTs) comprise two plates separated by either a vacuum or fluid gap. The plates are biased by a DC voltage and then superimposed with the AC signal of chosen frequency and amplitude. The working principle of CMUTs is based on Coulomb's laws of attraction. During the DC bias the electrostatic force and the mechanical restorative balance each other which keeps the membrane at the targeted displaced location. However, at a certain DC bias voltage, the electrostatic forces surpass the restorative force and the membrane touches the bottom electrode. For perfectly clamped CMUT plates, this physical phenomenon occurs at substantially $1/3^{rd}$ of the effective gap height. The distance is called pull-in or collapse distance and voltage at which the phenomenon happens is called collapse or pull-in voltage. One or more insulation layers may be sandwiched between the active membrane (top electrode), gap (vacuum or fluid) and the back-support structure (with bottom electrode) such that no short-circuit occurs during such collapse phenomenon.

The equation for collapsed voltage $V_{col}$ is shown below in Equations 1 and 2:

$$V_{col} = \sqrt{\frac{8Kg_{eff}^3}{27\varepsilon_0 A}} \quad \text{(Equation 1)}$$

where, K is membrane stiffness, $\varepsilon_0$ is permittivity of free space, and A is the device area. The effective gap height is given by:

$$g_{eff} = g_0 + \frac{t_r}{\varepsilon_r} \quad \text{(Equation 2)}$$

where $g_0$ is the vacuum/air gap, $t_r$ is the high contact resistance layer thickness, and $\varepsilon_r$ is the permittivity of the insulation material.

Accordingly, it can be seen that the bias voltage requirement of the CMUT that predominantly dominates the device sensitivity (transmit pressure in transmit mode) can be controlled by changing the effective gap height, keeping the other geometry parameters of a specific device constant.

There are applications where CMUTs are used in the collapse mode, however, in conventional mode the collapse phenomenon does impose some constraints to the DC displacement after the pull-in level, especially when higher DC stretching implies more linearity and higher-pressure during signal swing.

Figure 2:
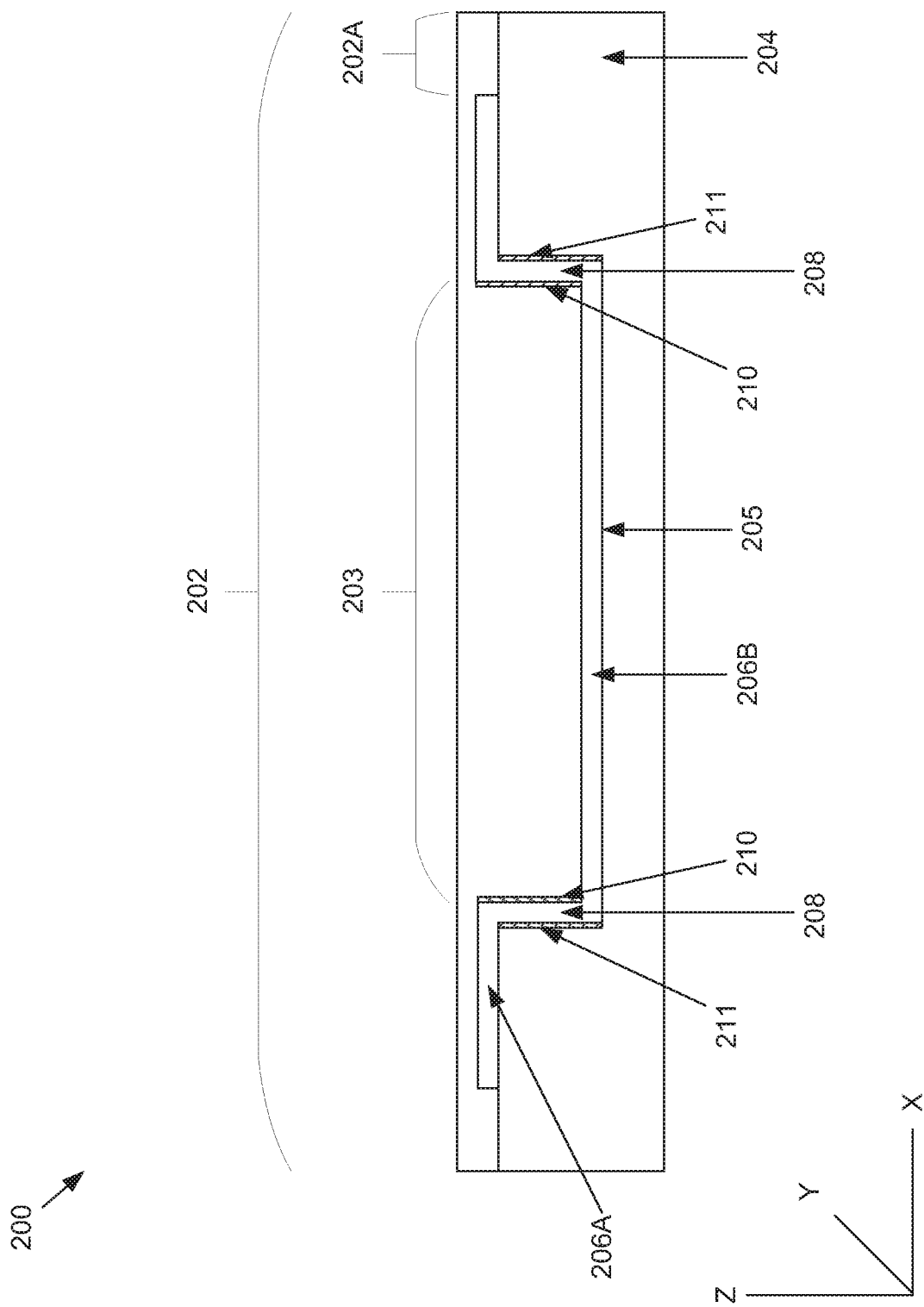
FIG. 2 illustrates a configuration for an example capacitive micromachined ultrasound transducer (CMUT) with non-coplanar actuation and displacement, in accordance with various embodiments.

FIG. 2 illustrates a configuration for an example capacitive micromachined ultrasound transducer (CMUT) with non-coplanar actuation and displacement, in accordance with various embodiments. Referring to FIG. 2, there is shown a CMUT 200 comprising a plate 202 and a substrate 204. The plate 202 may comprise a center mass 203. The center mass 203 protrudes down into a depression 205 in a corresponding area of the substrate 204. The substantially vertical edges of the center mass 203 comprise electrode(s) 210 and the substantially vertical edges of the depression 205 comprise electrode(s) 211. The electrodes 210 and 211 may be provided with electrical signals (DC bias and AC signal) used to move the plate 202 in the Z direction to generate sonic waves.

The plate 202 may be coupled to the substrate 204 at the outer perimeter area 202A of the plate 202. The coupling may be via any appropriate methods, including processes known in MEMS fabrication, such as, for example, wafer bonding.

It may be seen that the CMUT 200 has an upper vertical gap 206A and a lower vertical gap 206B between the plate 202 and the substrate 204. There is also a horizontal gap 208 between the electrodes 210 and 211. The horizontal gap 208 may be referred to as an electrode gap 208. The vertical gaps 206A and 206B are the actuation boundaries making the DC bias and the AC signal orthogonal to the device displacement direction along the Z axis. While not shown, when viewed from the top at the X-Y plane, the CMUT 200 may have a circular shape, a rectangular shape, or any other shape.

Since the CMUT plate 202 has a mechanical constraint in the X direction due to clamping at the edges (outer perimeter area 202A of the plate 202), the displacement degree of freedom may be predominantly in the Z direction. Accordingly, even though the actuation is in the X-direction, the X-direction displacement may be much less than the Z-direction displacement due to the mechanical constraint. Various embodiments of the disclosure may have, for example, a displacement ratio of 10 or more for Z-direction displacement versus X-direction displacement. It may be noted that the displacement ratio may be determined for specific usage for the CMUT 200.

Various parameters may be useful for determining the displacement ratio. The displacement ratio may depend on various variables (e.g., type of material used for the plate 202 and the substrate 204, the width of peripheral edge 202A, etc.). Some dimensions that may be useful for determining the displacement ration are discussed with respect to FIG. 3.

While an example configuration is shown in FIG. 2, as well as in other figures, it should be understood that the disclosure allows for various other configurations that may also be used for CMUTs.

The substantially vertical edges may be referred to as non-horizontal edges.

Figure 3:
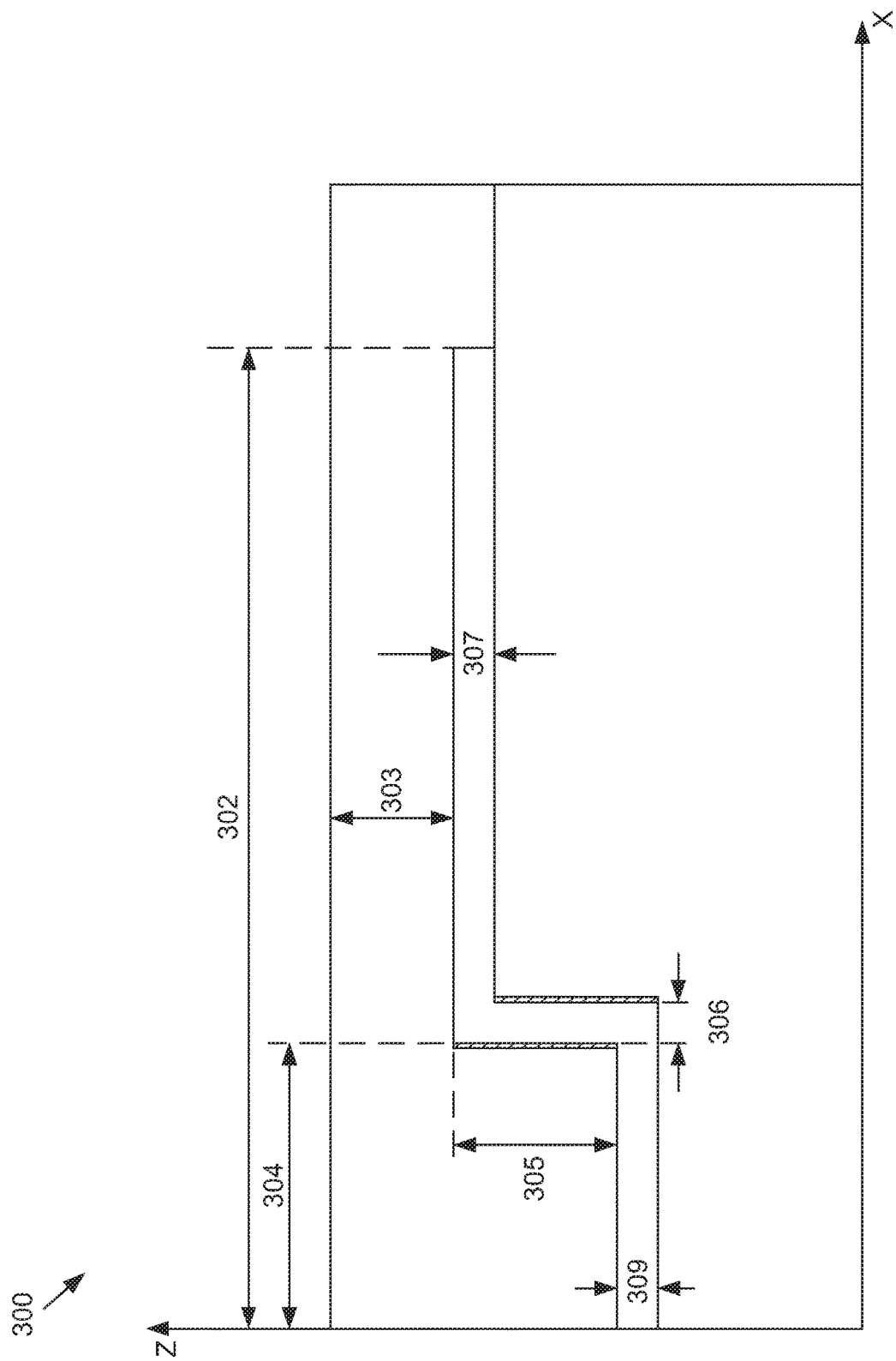
FIG. 3 illustrates example applicable dimensions of the example CMUT of FIG. 2, in accordance with various embodiments.

FIG. 3 illustrates example applicable dimensions of the example CMUT of FIG. 2, in accordance with various embodiments. Referring to FIG. 3, there is shown a partial view of a CMUT 300 that may be similar to the CMUT 200. The displacement ratio may use, for example, a plate radius ($P_r$) 302, a mass radius ($M_r$) 304, a horizontal gap ($G_h$) 306, vertical gaps ($G_v$) 307 and 309, a mass thickness ($M_t$) 305, and a plate thickness ($P_t$) 303. The horizontal gap 306 may be referred to as the electrode gap 306.

The vertical gaps ($G_v$) 307 and 309 may be equal to each other. The vertical gap ($G_v$) 307 and/or 309 may be equal to the horizontal gap ($G_h$) 306. The vertical gap ($G_v$) 307 and/or 309 may be greater than the horizontal gap ($G_h$) 306. The various gaps may be measured in any appropriate units such as, for example, microns, nanometers, etc.

A term "$E_{PI}$" may be a voltage for electrical pull-in, or the DC bias needed to make the electrodes collapse to each other in the X-direction. A term "$E_{MC}$" may be used for voltage needed for mechanical collapse. Mechanical collapse is defined as the phenomenon when at a certain DC bias the center mass 203 touches the bottom of the depression 205 of the substrate 204.

Various embodiments of the disclosure may keep the ratio $E_{PI}/E_{MC}$ to approximately, for example, 10 or more to allow for a full swing mechanical Z-displacement. Since the conductive electrodes 210 are at the edge of the center mass 203, there may not be a short circuit between the electrodes 210 and 211 even with a mechanical collapse. With $E_{PI}/E_{MC}$ at an example ratio of 10 or more, the electrical pull-in may not be expected to happen before the mechanical collapse. Thus, it may be seen that the ratio ($G_h/G_v$) for the horizontal gap to the vertical gap may define the electrical operating points of the CMUT. Additionally, since there is a smaller chance for the electrodes 210 and 211 to short circuit, the insulation layer(s) generally used in conventional CMUT structure may not be needed.

Figure 4:
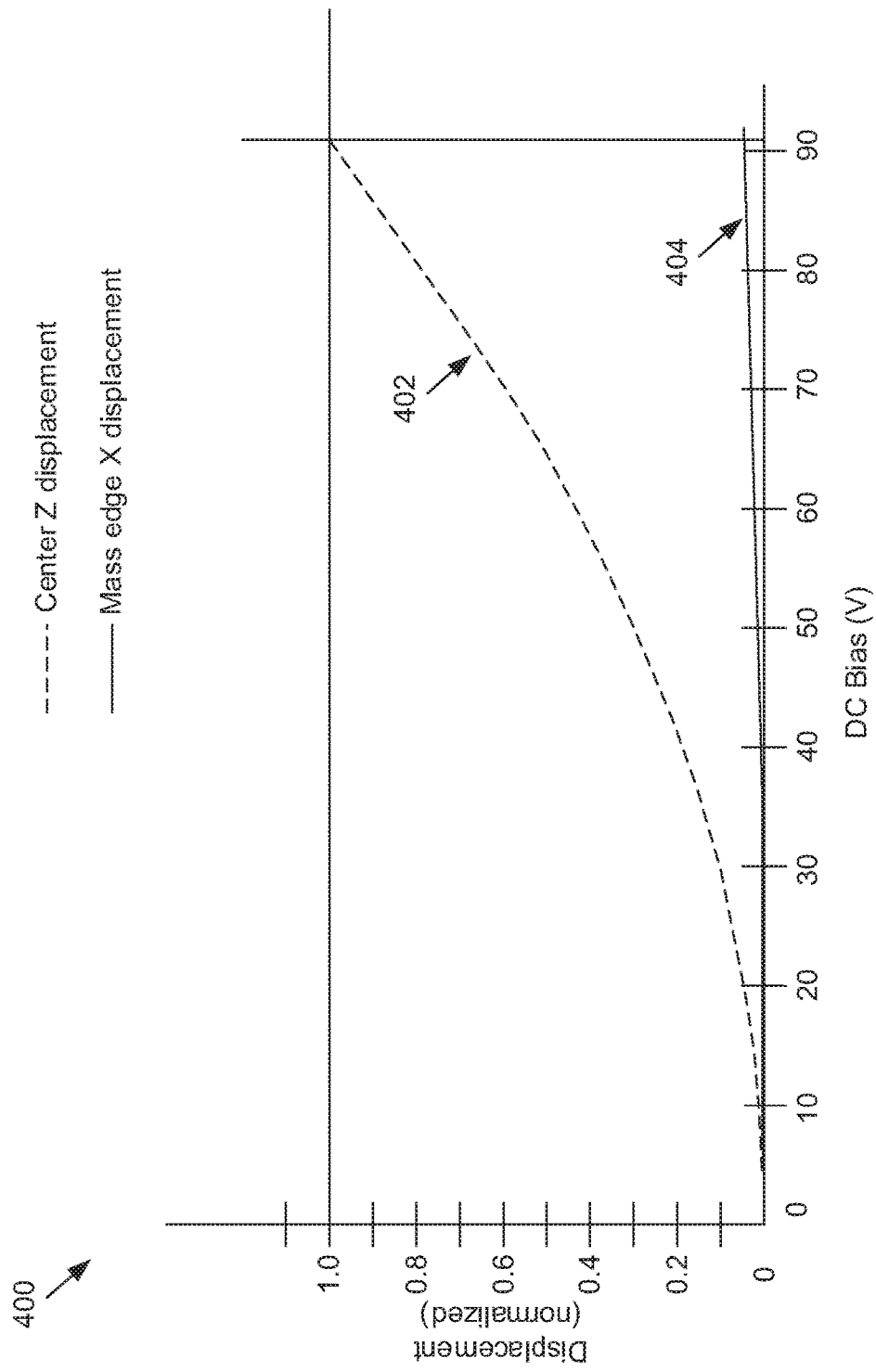
FIG. 4 illustrates an example graph of simulation of displacement for the example capacitive micromachined ultrasound transducer, in accordance with various embodiments.

FIG. 4 illustrates an example graph of simulation of displacement for the example capacitive micromachined ultrasound transducer, in accordance with various embodiments. Referring to FIG. 4, there is shown a graph 400 with DC bias in volts along the X-axis and normalized displacement along the Y-axis. Plot 402 shows the vertical gap ($G_v$) 309 at various voltages, and plot 404 shows the horizontal gap ($G_h$) 306 at various voltages. The design parameters for the simulation were set to:

plate radius ($P_r$) 302=100 um
mass radius ($M_r$) 304=$P_r$/3
vertical gaps ($G_v$) 307 and 309=1 normalized unit
horizontal gap ($G_h$) 306=$G_v$/5=0.2 normalized unit
mass thickness ($M_t$) 305=2*$G_v$
plate thickness ($P_t$) 303=1 um Based on the design parameters for the CMUT simulated in FIG. 4, each of the vertical gaps ($G_v$) 307 and 309 is 1 normalized unit, and the horizontal gap ($G_h$) 306 is 0.2 normalized unit. As can be seen from plot 402 of the graph 400, there is a mechanical collapse where the displacement of 1 normalized unit along the Z-axis occurs at a little more than 90 volts. At the same voltage, it can be seen from plot 404 that the displacement of the edge of the center mass 203 is about 0.05 normalized unit, which is much less than the horizontal gap of 0.2 normalized unit.

Accordingly, it can be seen that mechanical collapse without electrical pull-in clearly signifies the fact that a full DC induced stretch can be achieved without the conventional pull-in related problems such as, for example, short circuit, dielectric charging, etc. Accordingly, the various embodiments of the disclosure may be used as devices working in collapse, and, hence, may be able to provide wider bandwidth, added linearity, etc.

Figure 5:
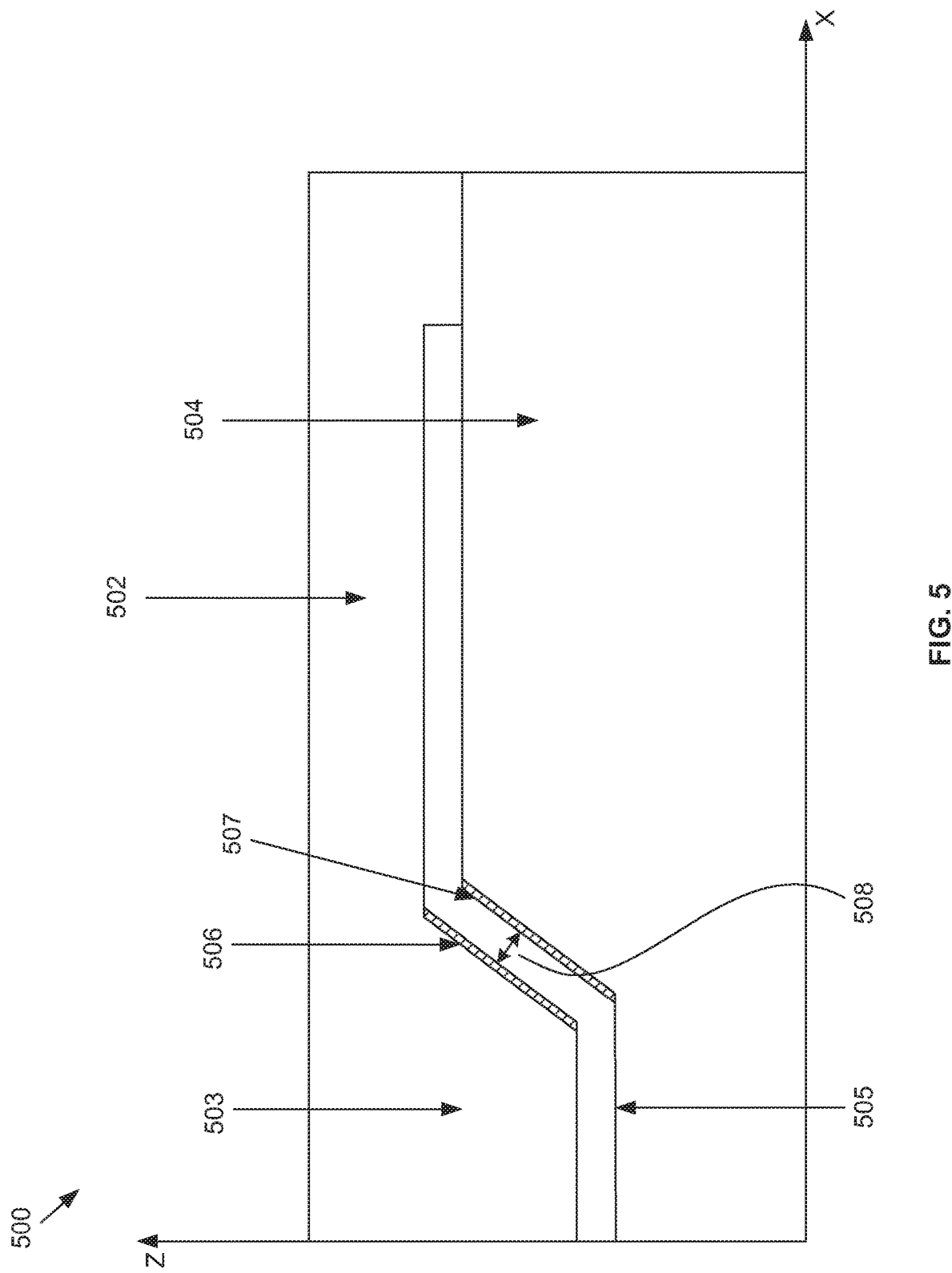
FIG. 5 illustrates another configuration for an example capacitive micromachined ultrasound transducer (CMUT) with non-coplanar actuation and displacement, in accordance with various embodiments.

FIG. 5 illustrates another configuration for an example capacitive micromachined ultrasound transducer (CMUT) with non-coplanar actuation and displacement, in accordance with various embodiments. Referring to FIG. 5, there is shown a CMUT 500 that is similar to the CMUT 200, except that the edges of the center mass 503 of the plate 502 and the edges of the depression 505 of the substrate 504 are diagonal. Accordingly, orientation of the electrodes 506 and 507 are also diagonal. The diagonal edges may also be referred to as non-horizontal edges where the angle of inclination may be between 0° and 90°. The orthogonal distance between the electrodes 506 and 507 may be referred to as the electrode gap 508.

Figure 6:
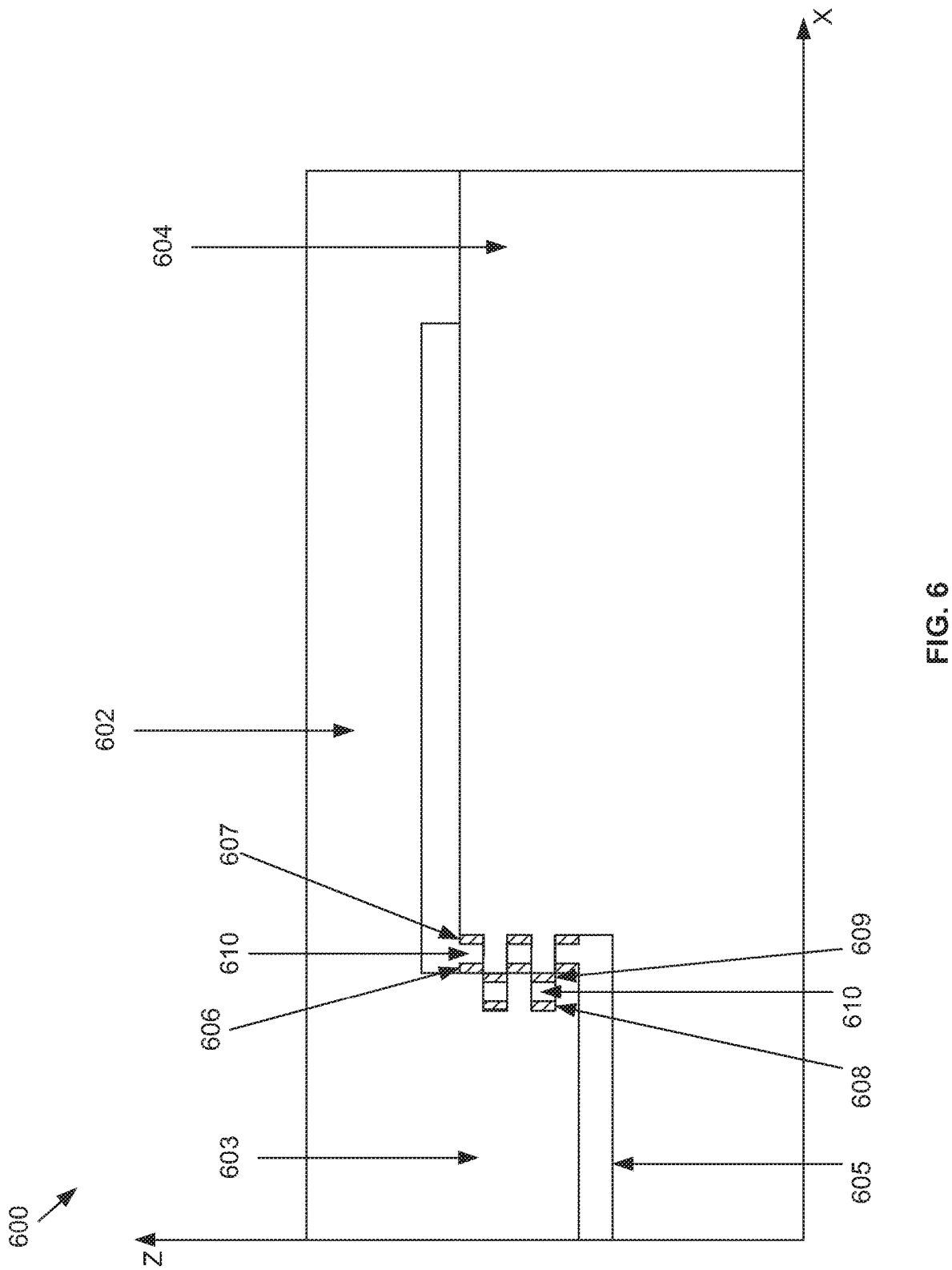
FIG. 6 illustrates another configuration for an example capacitive micromachined ultrasound transducer (CMUT) with non-coplanar actuation and displacement, in accordance with various embodiments.

FIG. 6 illustrates another configuration for an example capacitive micromachined ultrasound transducer (CMUT) with non-coplanar actuation and displacement, in accordance with various embodiments. Referring to FIG. 6, there is shown a CMUT 600 that is similar to the CMUT 200, except that the edges of the center mass 603 and the edges of the depression 605 are corrugated. Accordingly, the electrodes 606 and 607 are offset horizontally from the electrodes 608 and 609. There is a horizontal gap 610 between the electrodes 606 and 607 and between the electrodes 608 and 609. The horizontal gap 610 may be referred to as the electrode gap 610.

The corrugated edges may also be referred to as non-horizontal edges.

Figure 7:
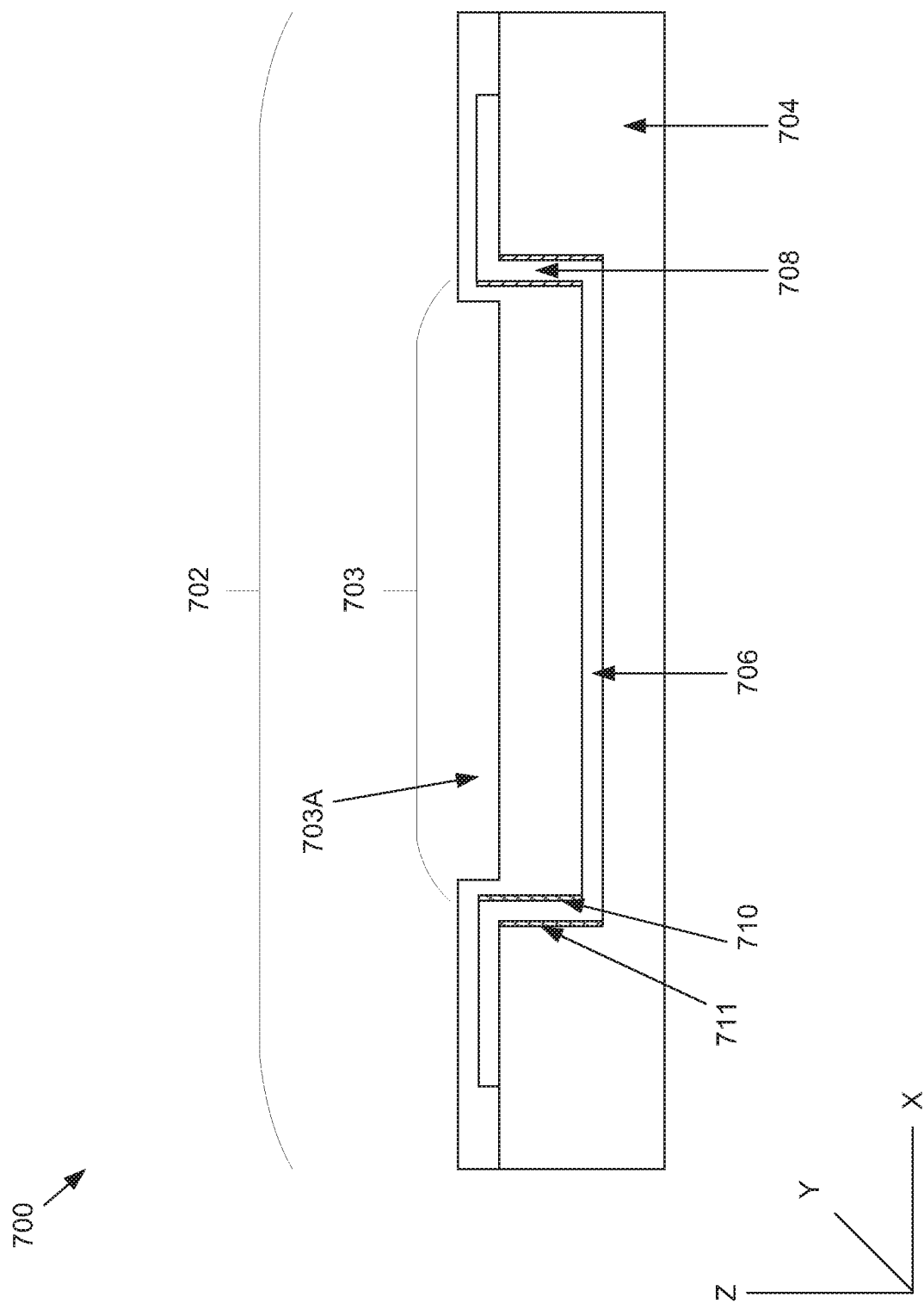
FIG. 7 illustrates another configuration for an example capacitive micromachined ultrasound transducer (CMUT) with non-coplanar actuation and displacement, in accordance with various embodiments.

FIG. 7 illustrates another configuration for an example capacitive micromachined ultrasound transducer (CMUT) with non-coplanar actuation and displacement, in accordance with various embodiments. Referring to FIG. 7, the CMUT 700 is similar to the CMUT 200. The CMUT 700 comprises a plate 702 with a center mass 703, and a substrate 704. There are electrodes 710 and 711 with a horizontal gap 708 and a vertical gap 706 between the plate 702 and the substrate 704.

The CMUT 700 also comprises a depression 703A in the center mass 703. The specific dimensions of the depression 703A may vary for various embodiments, and the shape of the depression 703A may be any of various shapes.

Figure 8:
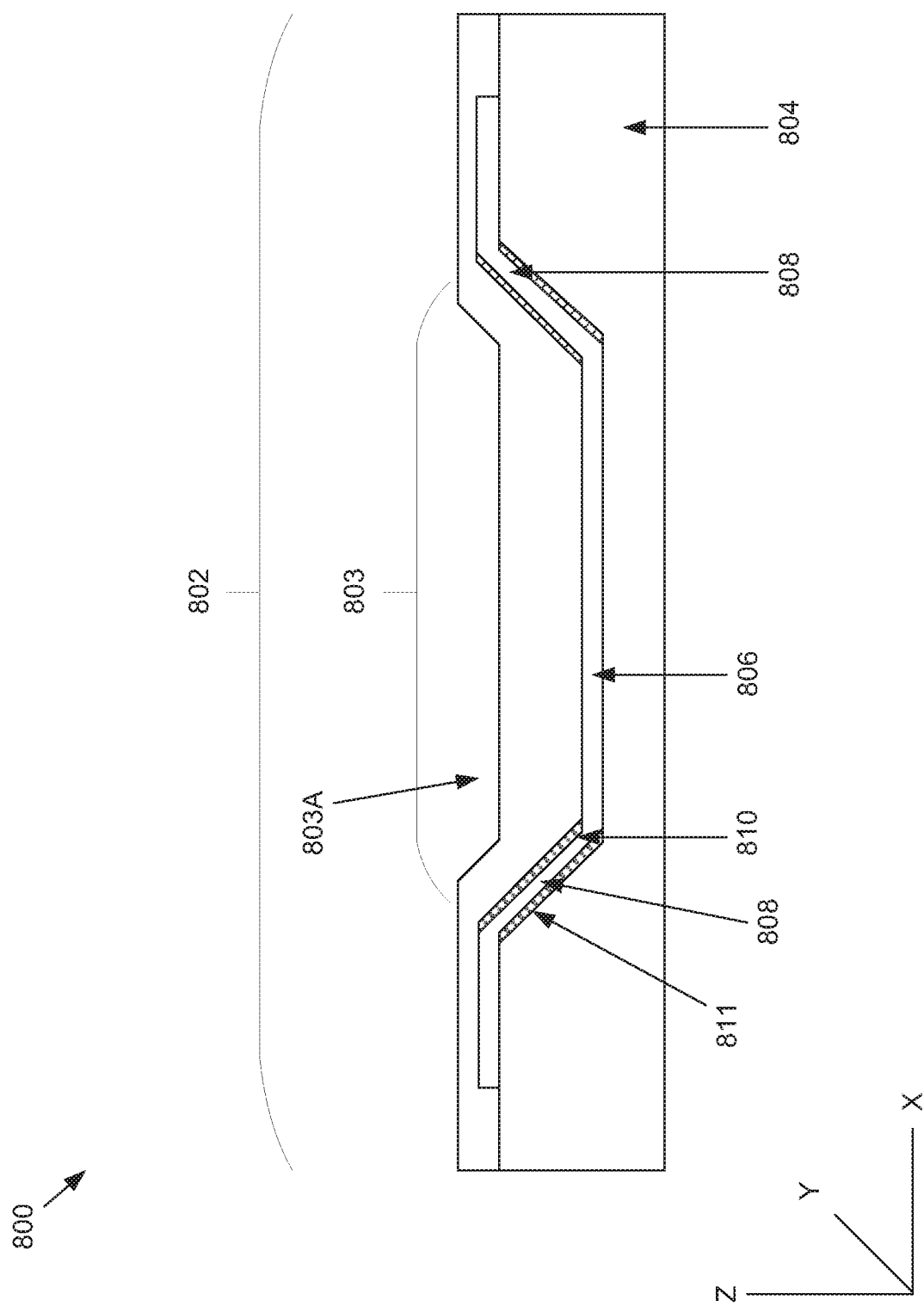
FIG. 8 illustrates another configuration for an example capacitive micromachined ultrasound transducer (CMUT) with non-coplanar actuation and displacement, in accordance with various embodiments.

FIG. 8 illustrates another configuration for an example capacitive micromachined ultrasound transducer (CMUT) with non-coplanar actuation and displacement, in accordance with various embodiments. Referring to FIG. 8, the CMUT 800 is similar to the CMUT 500. The CMUT 800 comprises a plate 802 with a center mass 803, and a substrate 804. There are electrodes 810 and 811 with a horizontal gap 808 and a vertical gap 806 between the plate 802 and the substrate 804.

The CMUT 800 also comprises a depression 803A in the center mass 803. The specific dimensions of the depression 803A may vary for various embodiments, and the shape of the depression 803A may be any of various shapes.

Figure 9:
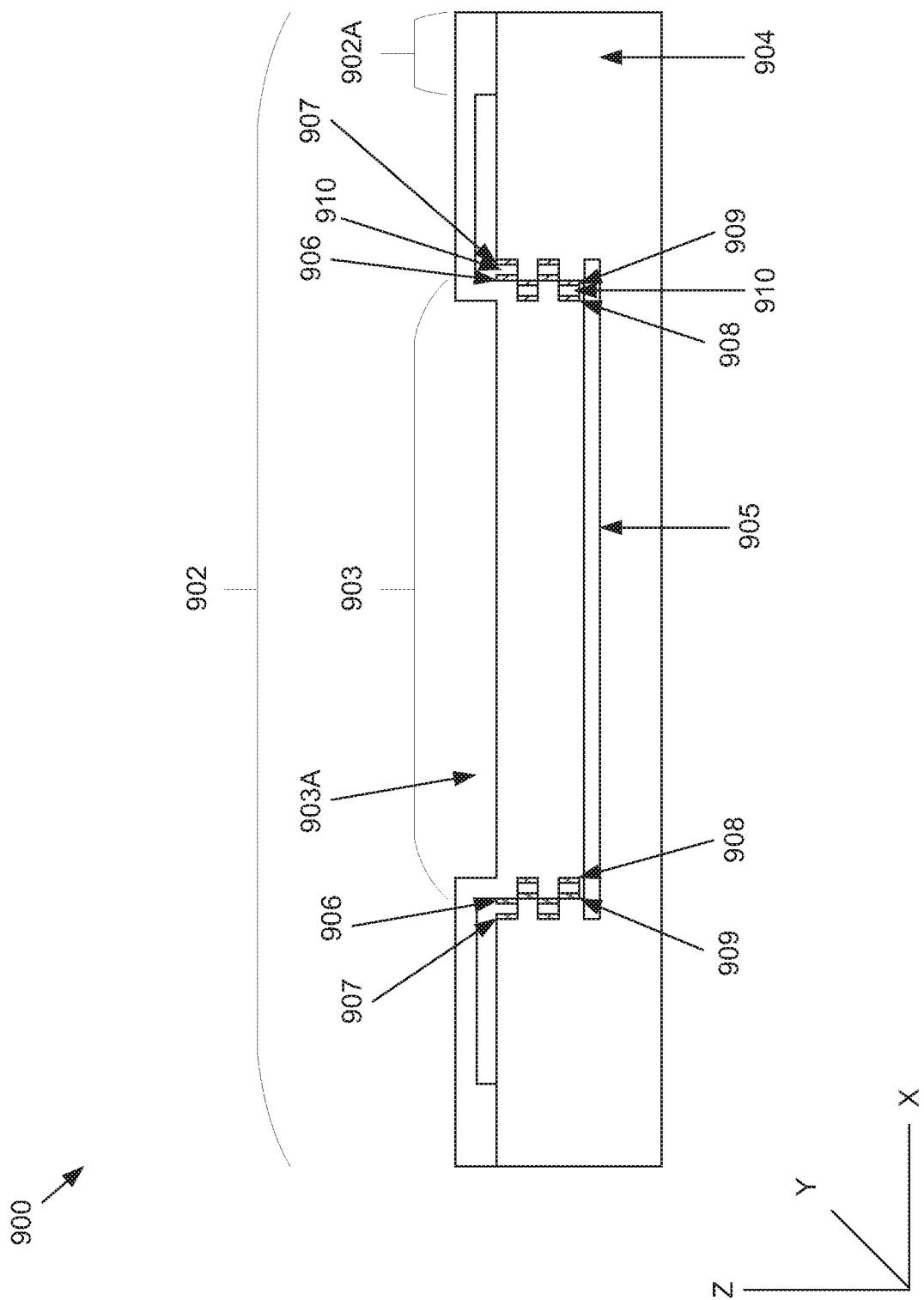
FIG. 9 illustrates another configuration for an example capacitive micromachined ultrasound transducer (CMUT) with non-coplanar actuation and displacement, in accordance with various embodiments.

FIG. 9 illustrates another configuration for an example capacitive micromachined ultrasound transducer (CMUT) with non-coplanar actuation and displacement, in accordance with various embodiments. Referring to FIG. 9, the CMUT 900 is similar to the CMUT 600. The CMUT 900 comprises a plate 902 with a center mass 903, and a substrate 904 with a depression 905. There are electrodes 906 and 907 with a horizontal gap 910, electrodes 908 and 909 with a horizontal gap 910.

The CMUT 900 also comprises a depression 903A in the center mass 903. The specific dimensions of the depression 903A may vary for various embodiments, and the shape of the depression 903A may be any of various shapes.

Figure 10:
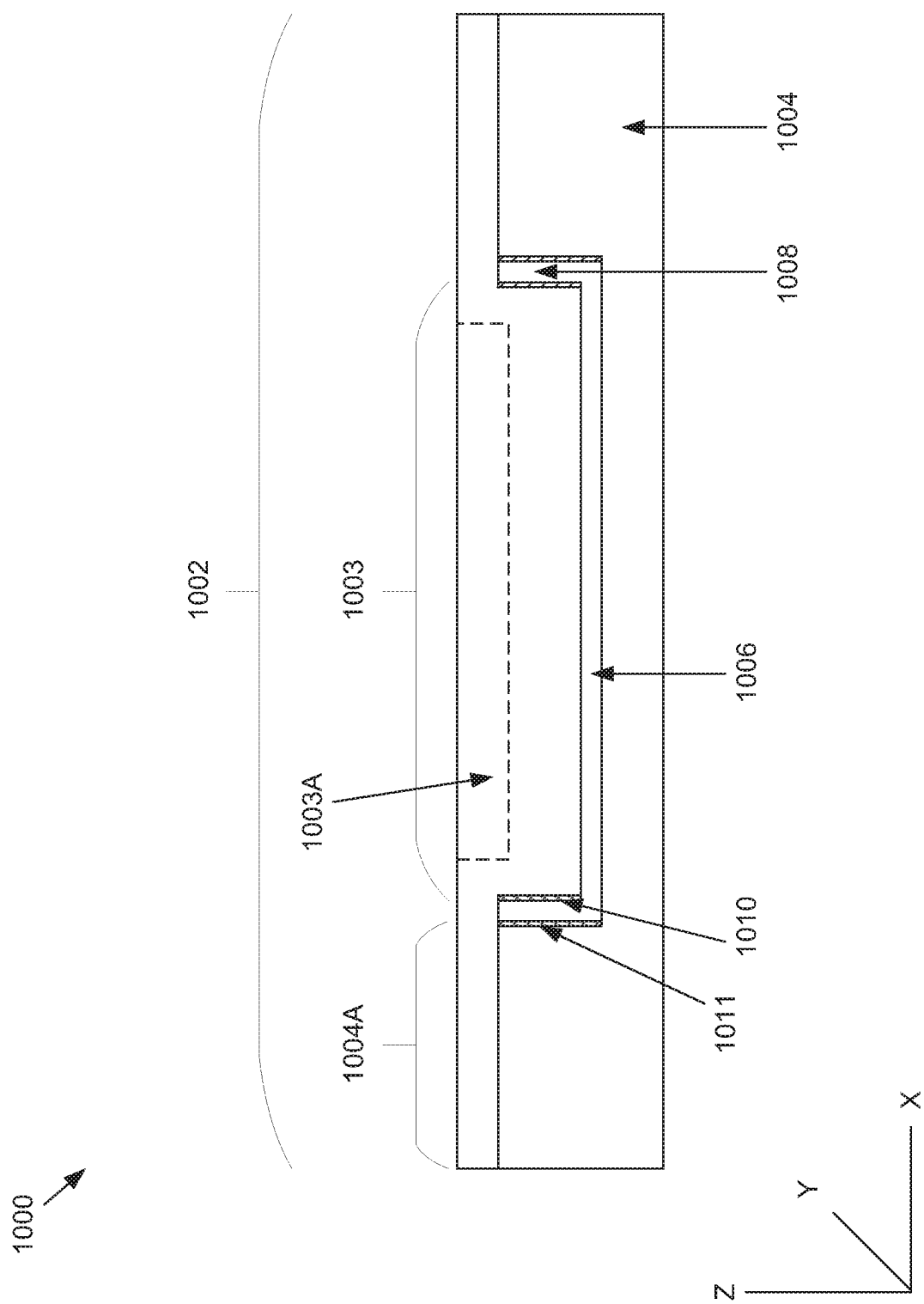
FIG. 10 illustrates another configuration for an example capacitive micromachined ultrasound transducer (CMUT) with non-coplanar actuation and displacement, in accordance with various embodiments.

FIG. 10 illustrates another configuration for an example capacitive micromachined ultrasound transducer (CMUT) with non-coplanar actuation and displacement, in accordance with various embodiments. Referring to FIG. 10, the CMUT 1000 is similar to the CMUT 200 or the CMUT 700 except that the plate 1002 is coupled to the substrate 1004 such that substantially an entire top surface of the substrate 1004 is coupled to a corresponding bottom surface of the plate 1002. There may be a depression 1003A in the center mass 1003 where the specific dimensions of the depression 1003A may vary for various embodiments, and the shape of the depression 1003A may be any of various shapes. There are electrodes 1010 and 1011 with a horizontal gap 1008, and a vertical gap 1006 between the plate 1002 and the substrate 1004.

Figure 11:
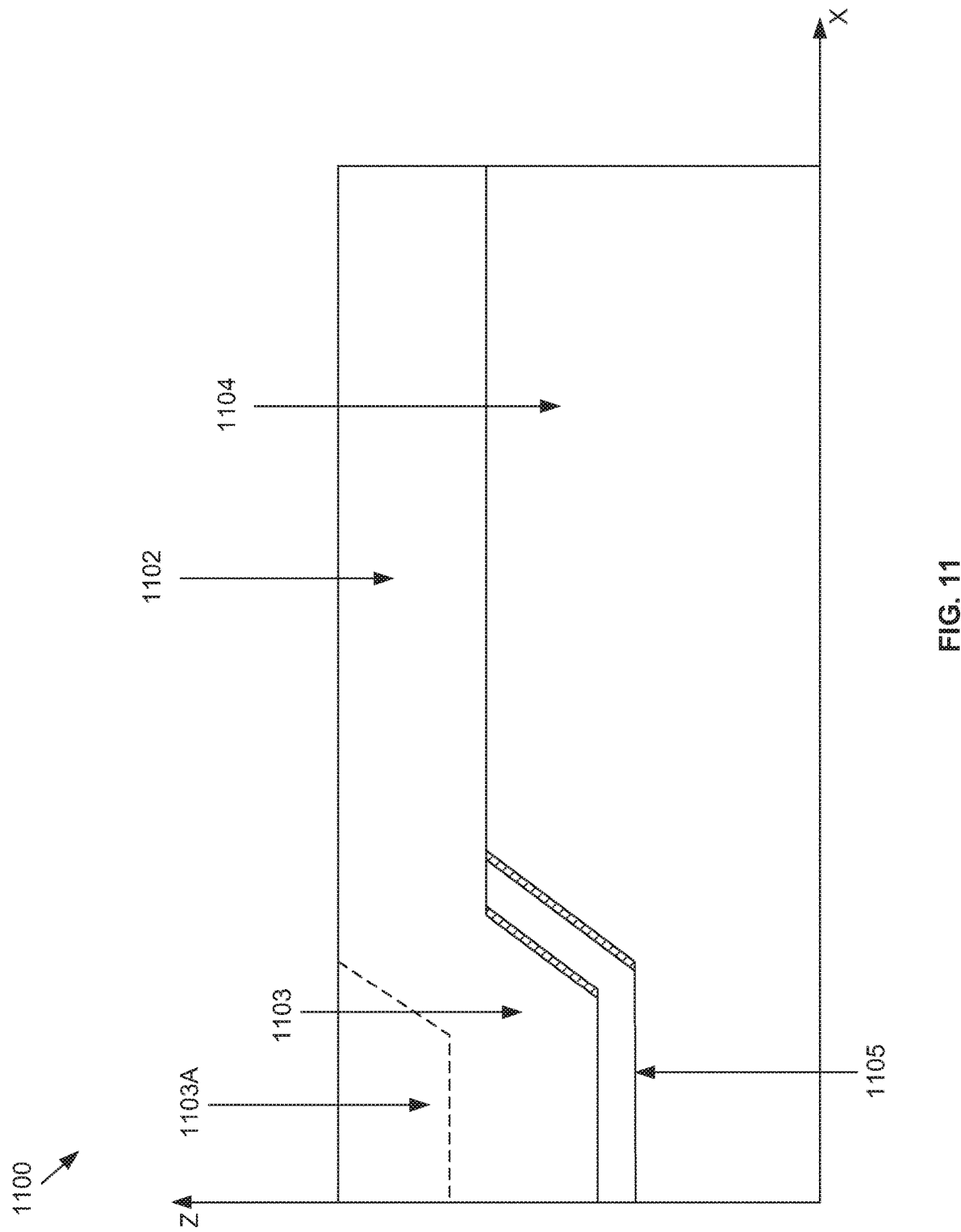
FIG. 11 illustrates another configuration for an example capacitive micromachined ultrasound transducer (CMUT) with non-coplanar actuation and displacement, in accordance with various embodiments.

FIG. 11 illustrates another configuration for an example capacitive micromachined ultrasound transducer (CMUT) with non-coplanar actuation and displacement, in accordance with various embodiments. Referring to FIG. 11, the CMUT 1100 is similar to the CMUT 500 or the CMUT 800. The CMUT 1100 comprises a plate 1102 with a center mass 1103 and the substrate 1104 with a depression 1105. The plate 1102 is coupled to the substrate 1104 such that substantially an entire top surface of the substrate 1104 is coupled to a corresponding bottom surface of the plate 1102. There may be a depression 1103A in the center mass 1103 where the specific dimensions of the depression 1103A may vary for various embodiments, and the shape of the depression 1103A may be any of various shapes.

Figure 12:
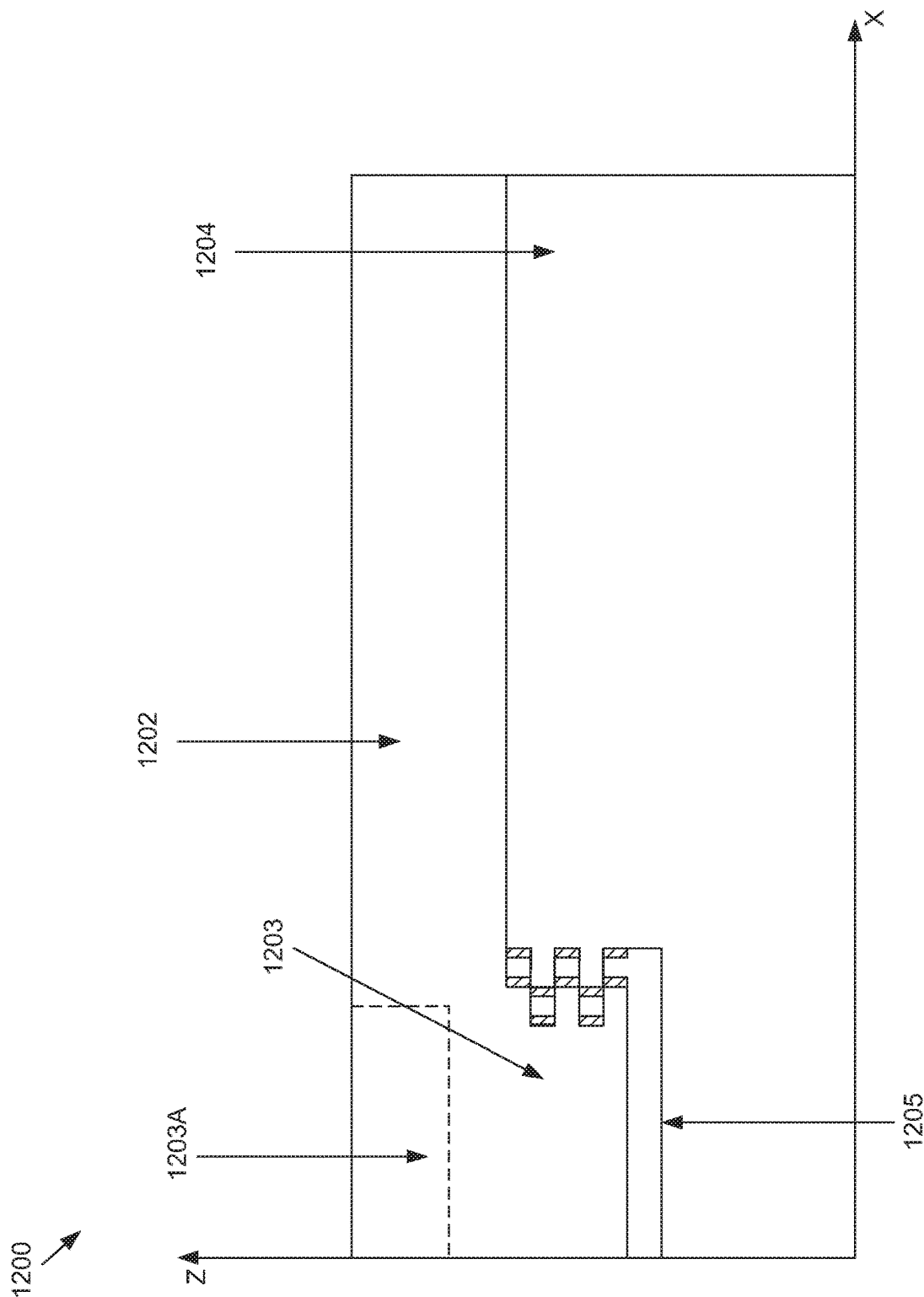
FIG. 12 illustrates another configuration for an example capacitive micromachined ultrasound transducer (CMUT) with non-coplanar actuation and displacement, in accordance with various embodiments.

FIG. 12 illustrates another configuration for an example capacitive micromachined ultrasound transducer (CMUT) with non-coplanar actuation and displacement, in accordance with various embodiments. Referring to FIG. 12, the CMUT 1200 is similar to the CMUT 600 or the CMUT 900. The CMUT 1200 comprises a plate 1202 with a center mass 1203 and the substrate 1204 with a depression 1205. The plate 1202 is coupled to the substrate 1204 such that substantially an entire top surface of the substrate 1204 is coupled to a corresponding bottom surface of the plate 1202. There may be a depression 1203A in the center mass 1203 where the specific dimensions of the depression 1203A may vary for various embodiments, and the shape of the depression 1203A may be any of various shapes.

Figure 13:
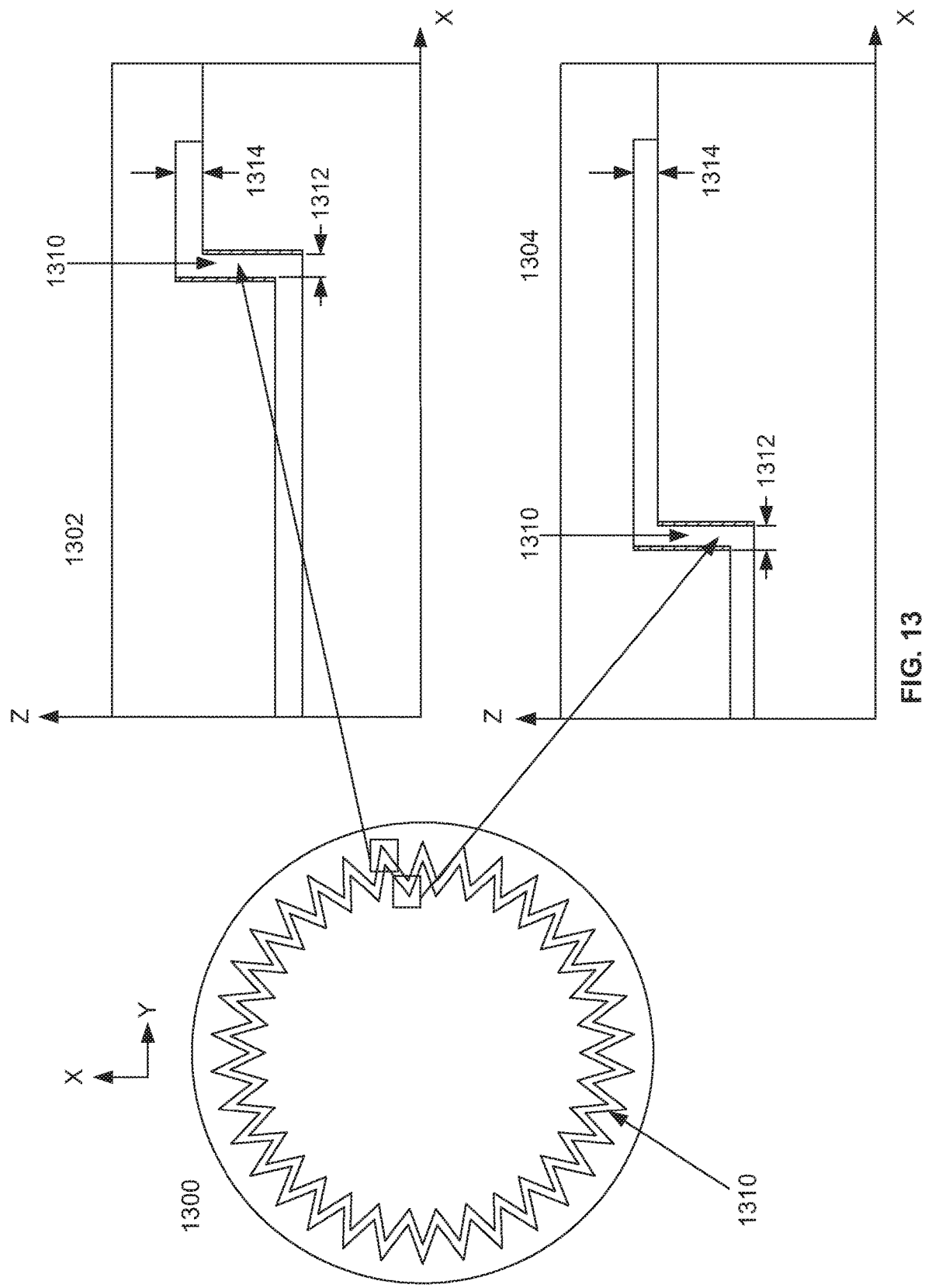
FIG. 13 illustrates another configuration for an example capacitive micromachined ultrasound transducer (CMUT) with non-coplanar actuation and displacement, in accordance with various embodiments.

FIG. 13 illustrates another configuration for an example capacitive micromachined ultrasound transducer (CMUT) with non-coplanar actuation and displacement, in accordance with various embodiments. Referring to FIG. 13, there is shown a top cross-sectional view (for example, X-Y plane) of a CMUT 1300 that shows a pattern of a horizontal gap 1310. There are also shown side cross-sectional views (for example, X-Z plane) 1302 and 1304 that show the horizontal gap 1312 between the electrodes, as well as the upper vertical gap 1314. The horizontal gap 1312 may be similar to the horizontal gap 306 in FIG. 3, and the upper vertical gap 1314 may be similar to the upper vertical gap 307 in FIG. 3.

As can be seen, the cross-sectional view 1302 is for an outer portion of the horizontal gap 1310, and the cross-sectional view 1304 is for an inner portion of the horizontal gap 1310.

FIG. 14 illustrates another configuration for an example capacitive micromachined ultrasound transducer (CMUT) with non-coplanar actuation and displacement, in accordance with various embodiments. Referring to FIG. 14, there is shown a top cross-sectional view (for example, X-Y plane) of a CMUT 1400 that shows a pattern of a horizontal gap 1410. There are also shown side cross-sectional views (for example, X-Z plane) 1402 and 1404 that show the horizontal gap 1412 between the electrodes, as well as the upper vertical gap 1414. The horizontal gap 1412 may be similar to the horizontal gap 306 in FIG. 3, and the upper vertical gap 1414 may be similar to the upper vertical gap 307 in FIG. 3.

As can be seen, the cross-sectional view 1402 is for an outer portion of the horizontal gap 1410, and the cross-sectional view 1404 is for an inner portion of the horizontal gap 1410.

While two example configurations are shown for increasing the total surface area of electrodes that can be used for the horizontal gaps 1310 and 1410 of the CMUTs 1300 and 1400, respectively, a horizontal gap when seen from the top (for example, X-Y plane) may be any of various shapes such as, for example, a circle, an oval, a regular or irregular polygon, etc. The horizontal gap may be, for example, continuous as shown in FIGS. 13 and 14, one or more discrete pieces that together do not go all the way around a CMUT, or one or more discrete pieces that together go around a CMUT. Accordingly, when viewed from above (for example, the X-Y plane), the horizontal gap of a CMUT may comprise one or more gaps, where each gap may be any geometric shape with any pattern.

Additionally, any CMUT may have any geometric shape when viewed from the top (for example, the X-Y plane). For example, while the CMUTs 1300 and 1400 are shown to be circular, a CMUT may be elliptical, oval, a polygon, etc. Additionally, while several configurations were shown, various embodiments of the disclosure need not be so limited. For example, the CMUT 200 may have multiple electrodes 210 and 211 similar to the CMUT 600. That is, while the edges may be planar, there may be multiple electrodes may be multiple electrodes 210 and corresponding multiple electrodes 211. Or there may be a different number of electrodes 210 than electrodes 211, where, for example, multiple electrodes 210 may be used for a single electrode 211 or vice versa.

Additionally, the center mass 203, 503, 603, 703, 803, 903, etc., may be different shapes than the examples disclosed. For example, the center mass 503 may have rounded (convex) edges and the depression 505 of the substrate 504 may have rounded (concave) edges so that the depression 505 may accept the center mass 503. Accordingly, various embodiments of the disclosure may have appropriately rounded electrodes 506 and 507.

However, the shape of a center mass and/or a depression of a substrate need not be limited to just what is mentioned in the disclosure. Rather, any appropriate shape may be used. Furthermore, the electrodes placed on the edge surfaces of a center mass and/or a depression may have conforming shapes to the edge surfaces or shapes that are different than the edge surfaces.

Additionally, while various descriptions were made of edges, surfaces, electrodes, the edge, surface, or electrode may be a single, continuous edge/surface/electrode. For example, when the center mass 203 is cylindrical, the center mass 203 may comprise a single vertical surface. Accordingly, there may be a single electrode 210 and a single electrode 211 for the CMUT 200. However, even when there is a single surface, there may be multiple electrodes 210 and multiple electrodes 211 placed at regular intervals along the single surface of the center mass 203 of the plate 202 and/or the single surface of the depression 205 of the substrate 204.

Furthermore, the gaps described in the various figures may be filled with fluid, such as, for example, air, or may comprise some level of vacuum. Accordingly, in various embodiments of the disclosure, the capacitive transducers may be configured such that the gaps are air-tight.

While various embodiments were disclosed with respect to capacitive micromachined ultrasound transducers, the disclosure may apply to other types of transducers other than ultrasound transducers. For example, a MEMS device that uses insulation layers may be able to use the disclosed embodiments to solve the problem of charging in one or more insulated layers. Also, while transducers were described in places as being used for medical imaging, various other types of imaging may also make use of the transducers. For example, imaging devices may be used for ultrasound/acoustic sensing, non-destructive evaluation (NDE), ultrasound therapy (High Intensity Focused Ultrasound (HIFU), etc.), etc., in addition to ultrasound imaging of humans, animals, etc.

Accordingly, as can be seen, the disclosure provides for a capacitive transducer comprising a plate comprising a protruding center mass, a substrate with a center depression configured to accept the center mass, a first electrode coupled to a non-horizontal edge surface of the center mass, and a second electrode coupled to a non-horizontal edge surface of the center depression. The plate may be coupled to the substrate at least along an outer perimeter area of the plate and the substrate.

The non-horizontal edge surface of the center mass and the non-horizontal edge surface of the center depression may be substantially vertical surfaces. The non-horizontal edge surface of the center mass and the non-horizontal edge surface of the center depression may be angled surfaces. The non-horizontal edge surface of the center mass and the non-horizontal edge surface of the center depression may be rounded surfaces. The non-horizontal edge surface of the center mass and the non-horizontal edge surface of the center depression may be corrugated surfaces.

At least a portion of a top surface of the center mass may not be coplanar with a portion of a top surface of the plate that is not the center mass. Substantially an entire top surface of the substrate may be coupled to a corresponding bottom surface of the plate.

There may be a first vertical gap between a bottom surface of the center mass and a bottom surface of the center depression, and there may be a second vertical gap between a non-center mass portion of the plate and a top surface of the substrate. There may be a horizontal gap between the first electrode and the second electrode. The first vertical gap may be equal to the second vertical gap. The horizontal gap may be equal to one or both of the first vertical gap and the second vertical gap.

The first vertical gap, the second vertical gap, and the horizontal gap may be filled with gas, such as, for example, air. The plate and the substrate may be configured to be coupled to form an air-tight barrier around the gap. The first vertical gap, the second vertical gap, and the horizontal gap may comprise a substantially gas-free vacuum.

Various embodiments of the disclosure may also provide for a capacitive transducer comprising a capacitive transducer, comprising a plate with a protruding center mass, a substrate with a center depression configured to accept the center mass, a first electrode coupled to a non-horizontal edge surface of the center mass; and a second electrode coupled to a non-horizontal edge surface of the center depression.

The plate may be coupled to the substrate at least along an outer perimeter area of the plate and the substrate, and the non-horizontal edge surface of the center mass and the non-horizontal edge surface of the center depression may be substantially vertical surfaces.

There may be a first vertical gap between a bottom surface of the center mass and a bottom surface of the center depression, and a second vertical gap between a non-center mass portion of the plate and a top surface of the substrate. There may be a horizontal gap between the first electrode and the second electrode. At least a portion of a top surface of the center mass is not coplanar with a portion of a top surface of the plate that is not the center mass.

Substantially an entire top surface of the substrate is coupled to a corresponding bottom surface of the plate, and the horizontal gap may be equal to one or both of the first vertical gap and the second vertical gap.

Various embodiments of the disclosure may further provide for a capacitive transducer comprising a plate comprising a protruding center mass, a substrate with a center depression configured to accept the center mass, a first electrode coupled to a non-horizontal edge surface of the center mass, and a second electrode coupled to a non-horizontal edge surface of the center depression.

The plate may be coupled to the substrate at least along an outer perimeter area of the plate and the substrate, the non-horizontal edge surface of the center mass and the non-horizontal edge surface of the center depression may be substantially vertical surfaces, and at least a portion of a top surface of the center mass is not coplanar with a portion of a top surface of the plate that is not the center mass. Substantially an entire top surface of the substrate may be coupled to a corresponding bottom surface of the plate.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set $\{(x), (y), (x, y)\}$. As another example, "x, y, and/or z" means any element of the seven-element set $\{(x), (y), (z), (x, y), (x, z), (y, z), (x, y, z)\}$. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What are claimed:

1. A capacitive transducer, comprising:
   a plate comprising a protruding center mass;
   a substrate with a center depression configured to accept the center mass;
   a first electrode coupled to a non-horizontal edge surface of the center mass; and
   a second electrode coupled to a non-horizontal edge surface of the center depression,
   wherein the plate is directly coupled to the substrate at least along an outer perimeter area of the plate and the substrate, and
   wherein there is a vertical gap between a non-center mass portion of the plate and an uppermost surface of the substrate.

2. The capacitive transducer of claim 1, wherein the non-horizontal edge surface of the center mass and the non-horizontal edge surface of the center depression are substantially vertical surfaces.

3. The capacitive transducer of claim 1, wherein the non-horizontal edge surface of the center mass and the non-horizontal edge surface of the center depression are angled surfaces.

4. The capacitive transducer of claim 1, wherein the non-horizontal edge surface of the center mass and the non-horizontal edge surface of the center depression are rounded surfaces.

5. The capacitive transducer of claim 1, wherein the non-horizontal edge surface of the center mass and the non-horizontal edge surface of the center depression are corrugated surfaces.

6. The capacitive transducer of claim 1, wherein, at rest in a non-collapsed state, at least a portion of a top planar surface of the center mass is not coplanar with a portion of a top planar surface of the plate that is not the center mass.

7. The capacitive transducer of claim 1, wherein substantially an entire top surface of the substrate is coupled to a corresponding bottom surface of the plate.

8. The capacitive transducer of claim 1, wherein:
   there is an additional vertical gap between a bottom surface of the center mass and a bottom surface of the center depression; and
   there is a horizontal gap between the first electrode and the second electrode.

9. The capacitive transducer of claim 8, wherein the vertical gap is equal to the additional vertical gap.

10. The capacitive transducer of claim 8, wherein the horizontal gap is equal to one or both of the vertical gap and the additional vertical gap.

11. The capacitive transducer of claim 8, wherein the vertical gap, the additional vertical gap, and the horizontal gap are filled with gas.

12. The capacitive transducer of claim 8, wherein the vertical gap, the additional vertical gap, and the horizontal gap are filled with air.

13. The capacitive transducer of claim 8, wherein the plate and the substrate are configured to be coupled to form an air-tight barrier around the gap.

14. The capacitive transducer of claim 13, wherein the vertical gap, the additional vertical gap, and the horizontal gap comprises a substantially gas-free vacuum.

15. A capacitive transducer, comprising:
   a plate comprising a protruding center mass;
   a substrate with a center depression configured to accept the center mass;
   a first electrode coupled to a non-horizontal edge surface of the center mass; and
   a second electrode coupled to a non-horizontal edge surface of the center depression,
   wherein:
   the plate is coupled to the substrate at least along an outer perimeter area of the plate and the substrate,
   the non-horizontal edge surface of the center mass and the non-horizontal edge surface of the center depression are substantially vertical surfaces,
   there is a first vertical gap between a bottom surface of the center mass and a bottom surface of the center depression,
   there is a second vertical gap between a non-center mass portion of the plate and an uppermost surface of the substrate, and
   there is a horizontal gap between the first electrode and the second electrode.

16. The capacitive transducer of claim 15, wherein, at rest in a non-collapsed state, at least a portion of a top planar surface of the center mass is not coplanar with a portion of a top planar surface of the plate that is not the center mass.

17. The capacitive transducer of claim 15, wherein substantially an entire top surface of the substrate is coupled to a corresponding bottom surface of the plate.

18. The capacitive transducer of claim 15, wherein the horizontal gap is equal to one or both of the first vertical gap and the second vertical gap.

19. A capacitive transducer, comprising:
   a plate comprising a top side and a bottom side, wherein:
   the bottom side comprises a protruding center mass,
   the top side comprises an indent above the protruding center mass, and
   a first thickness of the plate between the top side and the bottom side at the indent and the protruding center mass is greater than a second thickness of the plate between the top side and the bottom side outside of the indent and the protruding center mass;
   a substrate with a center depression configured to accept the center mass;
   a first electrode coupled to a non-horizontal edge surface of the center mass; and
   a second electrode coupled to a non-horizontal edge surface of the center depression,
   wherein:
   the plate is coupled to the substrate at least along an outer perimeter area of the plate and the substrate, and
   the non-horizontal edge surface of the center mass and the non-horizontal edge surface of the center depression are substantially vertical surfaces.

20. The capacitive transducer of claim 19, wherein substantially an entire top surface of the substrate is coupled to a corresponding bottom surface of the plate.

* * * * *